(12) United States Patent
Wickstrom

(10) Patent No.: US 8,460,225 B2
(45) Date of Patent: Jun. 11, 2013

(54) WEIGHT SHIFTING APPARATUS FOR AN ORTHOPEDIC SLING

(76) Inventor: Christopher Michael Wickstrom, Fort Myers, FL (US)

( * ) Notice: Subject to any disclaimer, the term of this patent is extended or adjusted under 35 U.S.C. 154(b) by 102 days.

(21) Appl. No.: 12/380,824

(22) Filed: Mar. 4, 2009

(65) Prior Publication Data

US 2010/0160842 A1    Jun. 24, 2010

Related U.S. Application Data

(60) Provisional application No. 61/068,113, filed on Mar. 4, 2008.

(51) Int. Cl.
*A61F 5/00* (2006.01)

(52) U.S. Cl.
USPC .............................................................. 602/4

(58) Field of Classification Search
USPC .............. 602/20, 3, 12, 60, 61, 62, 4; 128/46, 128/869, 874, 875, 876, 878, DIG. 15; 24/182, 24/31 V, 3.2; 224/150, 913; D24/190
See application file for complete search history.

(56) References Cited

U.S. PATENT DOCUMENTS

| | | | |
|---|---|---|---|
| 6,461,319 B1 * | 10/2002 | Ekey | 602/62 |
| 6,485,445 B1 * | 11/2002 | Hiltner | 602/4 |
| 6,709,411 B1 * | 3/2004 | Olinger | 602/4 |
| 2002/0029406 A1 * | 3/2002 | Meyer | 2/310 |
| 2006/0129075 A1 * | 6/2006 | Scheinberg et al. | 602/6 |
| 2008/0228116 A1 * | 9/2008 | Walker | 602/4 |

* cited by examiner

*Primary Examiner* — Patricia Bianco
*Assistant Examiner* — Caitlin Carreiro
(74) *Attorney, Agent, or Firm* — William E. Noonan

(57) ABSTRACT

An apparatus for laterally constraining the shoulder strap of an arm supporting orthopedic sling includes an armband for encircling and attaching to the well arm of the wearer and an anchor strap interconnected between the armband and the shoulder strap for pulling the shoulder strap laterally away from the wearer's neck and holding that strap such that the weight of the supported arm is borne at least primarily by the shoulder rather than the neck.

15 Claims, 7 Drawing Sheets

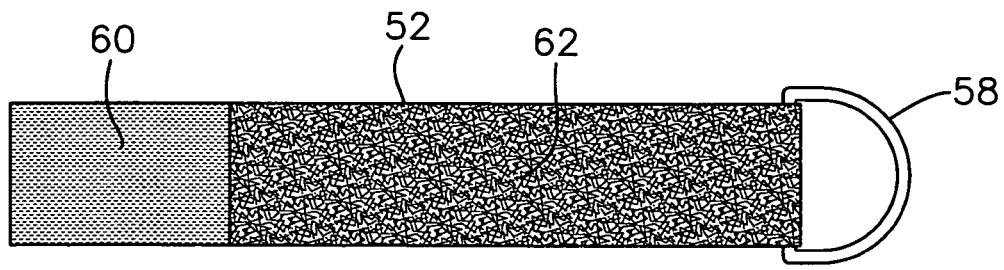
Fig. 3
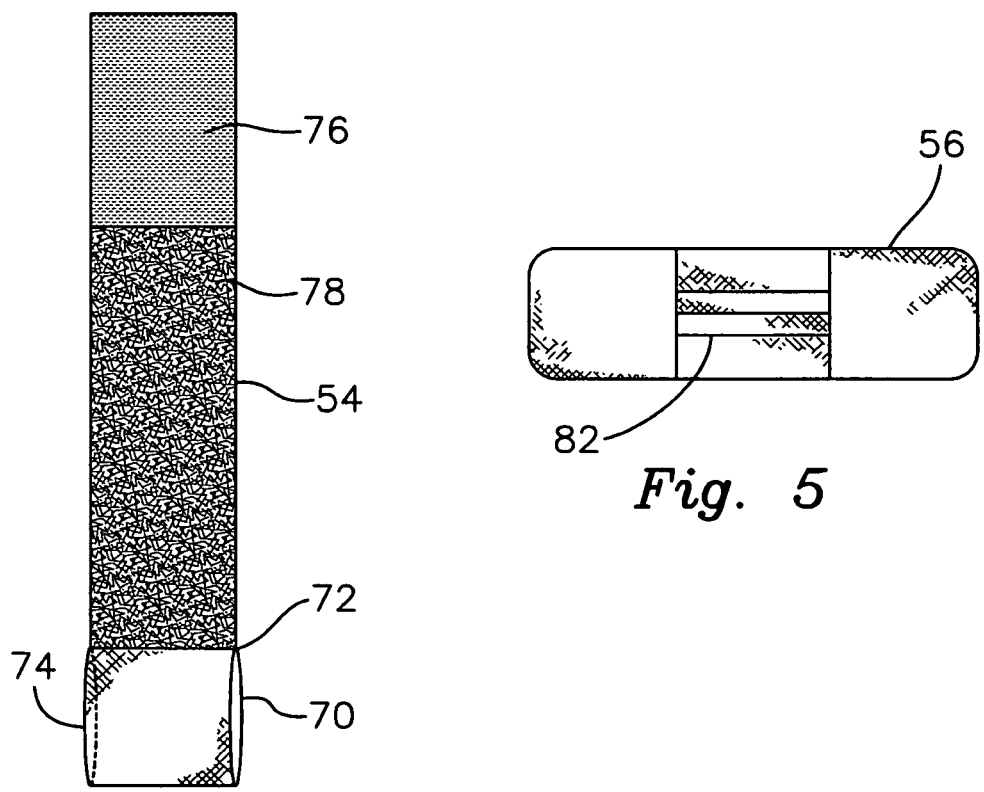
Fig. 4
Fig. 5

WEIGHT SHIFTING APPARATUS FOR AN ORTHOPEDIC SLING

RELATED APPLICATION

This application claims the benefit of U.S. Provisional Patent Application Ser. No. 61/068,113 filed Mar. 4, 2008.

FIELD OF THE INVENTION

This invention relates to an apparatus for shifting or transferring the weight of an arm supported by an orthopedic sling so that such weight is borne largely by the shoulder rather than the neck of the wearer.

BACKGROUND OF THE INVENTION

Orthopedic slings have long been used to support a broken or otherwise injured arm. Such slings are also commonly utilized to support the arm in cases where the wearer has injured his or her shoulder, elbow, wrist or hand. Most orthopedic slings feature an elongate strap that is wrapped over the shoulder opposite the supported arm (i.e. the "well shoulder"). Unfortunately, this type of medical product exhibits a common and extremely annoying problem. The weight of the supported arm, which is often compounded by a cast, bandages, etc., typically causes the strap of the sling to exert a large amount of localized pressure against the wearer's neck and, in particular, the trapezius muscle. This can cause the patient significant discomfort and result in neck pulls, strains and fatigue, as well as unwanted pressure on the carotid artery.

A number of slings have incorporated a cushioning pad in an attempt to alleviate the pressure exerted by the sling upon the wearer's neck. Although such pads have provided some relief, they are still not satisfactorily addressing the problem.

Various products, including those disclosed by U.S. Pat. Nos. 5,413,552 and 7,037,281, attempt to transfer the weight of the supported arm from the neck to the well shoulder. However, these products are unduly cumbersome and quite uncomfortable to wear. They also tend to greatly restrict the patient's ability to move his or her torso. Donahoo, U.S. Pat. No. 4,564,008, discloses a weight shifting apparatus incorporated integrally into the sling. That product is not adaptable for use with the vast majority of standard orthopedic slings already on the market.

SUMMARY OF THE INVENTION

It is therefore an object of the present invention to provide an apparatus for simply and conveniently transferring the weight and resulting pressure exerted by an orthopedic sling and supported arm from the neck to the well shoulder of the wearer.

It is a further object of this invention to provide a weight shifting constraint apparatus for an orthopedic sling that is extremely comfortable to wear and which does not interfere with movement of the wearer's well arm or torso.

It is a further object of this invention to provide a weight shifting constraint apparatus for an orthopedic sling that is quick, easy and convenient to put on and remove as needed.

It is a further object of this invention to provide a weight shifting constraint apparatus for an orthopedic sling that effectively reduces the neck pain, discomfort and other physical problems commonly associated with the use of an orthopedic sling.

It is a further object of this invention to provide a weight shifting or transferring constraint apparatus that may be used effectively and conveniently with virtually all types of orthopedic slings, as well as most known forms of orthopedic sling construction.

It is a further object of this invention to provide a weight shifting constraint apparatus for an orthopedic sling that is simpler and less expensive to manufacture than known devices of this type and which is far less cumbersome for the patient to wear and use.

It is a further object of this invention to provide a weight shifting constraint apparatus for an orthopedic sling, which is quickly and conveniently adjustable by either the patient, a caretaker or medical personnel, and which can be used effectively by a person of virtually any size or body type.

This invention results from a realization that the weight exerted by an orthopedic sling and supported arm may be effectively shifted from the the area of the trapezius muscle within the neck to the typically stronger shoulder muscles of the wearer by employing an apparatus that is attached to the wearer's well arm for pulling the sling strap laterally to a desired position on the shoulder. Such a construction effectively transfers the weight of the supported arm so that undesirable and uncomfortable pressure on the neck is reduced without requiring an unduly complex apparatus and without interfering with use of the wearer's well arm or torso.

This invention features an apparatus for constraining the shoulder strap of an orthopedic sling that supports an arm. The shoulder strap extends across the shoulder associated with the opposite, well arm of the wearer. The apparatus includes an armband for encircling and attaching to the well arm of the wearer. An anchor strap is interconnected between the armband and the shoulder strap of the orthopedic sling for pulling the sling strap laterally away from the neck of the wearer and holding the sling strap such that at least a majority of the weight of the supported arm is borne by the shoulder associated with the well arm rather than the neck of the wearer.

In a preferred embodiment, the apparatus further includes a cushioning pad component for attaching to the shoulder strap of the orthopedic sling and engaging the shoulder of the wearer's well arm. Means may be provided for fastening the anchoring strap to the cushioning pad. Such means may include a fastening loop carried by the cushioning pad. The anchor strap may be insertable through the fastening loop and may carry complementary first and second connectors that are interengaged to define an upper loop in the anchor strap. The upper loop in the anchor strap interengages the fastening loop carried by the cushioning pad to interconnect the anchor strap to the cushioning pad.

The armband may include complementary connective components that are interengaged to secure the armband about a wearer's well arm. One end of the armband may carry a fastening ring through which the opposite end of the armband is inserted and pulled in a reverse direction to tighten the armband about the wearer's well arm. The complementary connective components carried by the armband may include complementary hook and loop (i.e. Velcro®) connectors. Likewise, the first and second connectors carried by the anchor strap may include complementary hook and loop connectors.

The armband may be connected to the anchor strap by a sleeve that is carried by a lower end of the anchor strap. The armband may be inserted longitudinally through the sleeve such that the anchor strap is adjustable longitudinally along the armband.

In alternative embodiments, the anchoring strap may wrap about the shoulder strap of the sling and be releasably secured to itself by means of complementary hook and loop connectors to define an upper loop. In such versions, the upper loop receives the shoulder strap of the sling to attach the anchor strap to the shoulder strap. The anchor strap may itself be secured to the armband by hook and loop fasteners or other types of complementary connectors carried by the armband and the anchoring strap respectively.

DETAILED DESCRIPTION OF PREFERRED EMBODIMENTS

Other objects, features and advantages will occur from the following description of a preferred embodiment and the accompanying drawings, in which:

FIG. 3 is a top plan view of the armband;

FIG. 4 is a top plan view of the anchor strap;

FIG. 5 is a top plan view of the cushioning pad;

Figure 1:
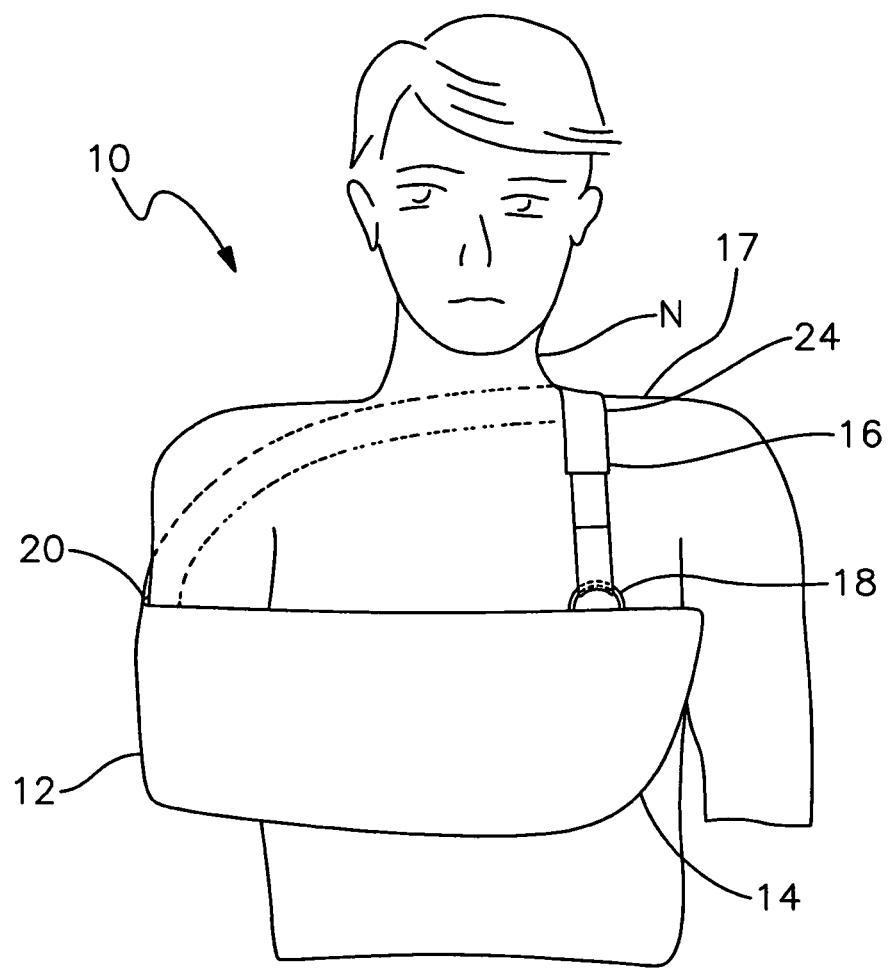
FIG. 1 is a front elevational view of a patient wearing a conventional orthopedic sling in accordance with the prior art.

There is shown in FIG. 1 a patient 10 whose injured arm is supported in a conventional manner by a known orthopedic sling 12. It should be understood that the sling is currently available in a wide variety of makes and models. As will be well known to persons skilled in the art, the patient's injured right arm is bent and supported in a pouch 14 of sling 12. A shoulder strap 16 extends through a support ring 18 attached to an upper edge of pouch 14. The lower end of strap 16 is wrapped about the ring 18 and secured to itself, in a manner not shown in detail, by a conventional two-part connector comprising, for example, hook and loop material (Velcro®). Shoulder strap 16 extends generally over the wearer's well shoulder 17 and across the wearer's back. The opposite end of strap 16 is secured through a second support ring 20 carried by the upper edge of pouch 14. Each end of the shoulder strap may be secured through a respective support ring in an analogous fashion, which will be known to persons skilled in the art. It should be well understood that various other conventional constructions may be employed by the sling.

As previously discussed, sling 12 and, in particular, shoulder strap 16 tend to become quite uncomfortable, particularly after extended use. Strap 16 is pulled, largely by the weight of the patient's supported right arm, against the side of the patient's neck N. This exerts pressure against the area of the trapezius muscle in the neck. At a minimum, this can create serious discomfort. Even worse, it can cause neck strain, sprains and unwanted pressure against the wearer's carotid artery. Various types of cushioning pads such as pad 24 have been installed on strap 16. Often, the cushioning pad comprises a sleeve that slides onto and along the shoulder strap. Although such pads do reduce the pressure somewhat, a significant amount of pressure and discomfort nonetheless accompany usage of sling 12.

Figure 2:
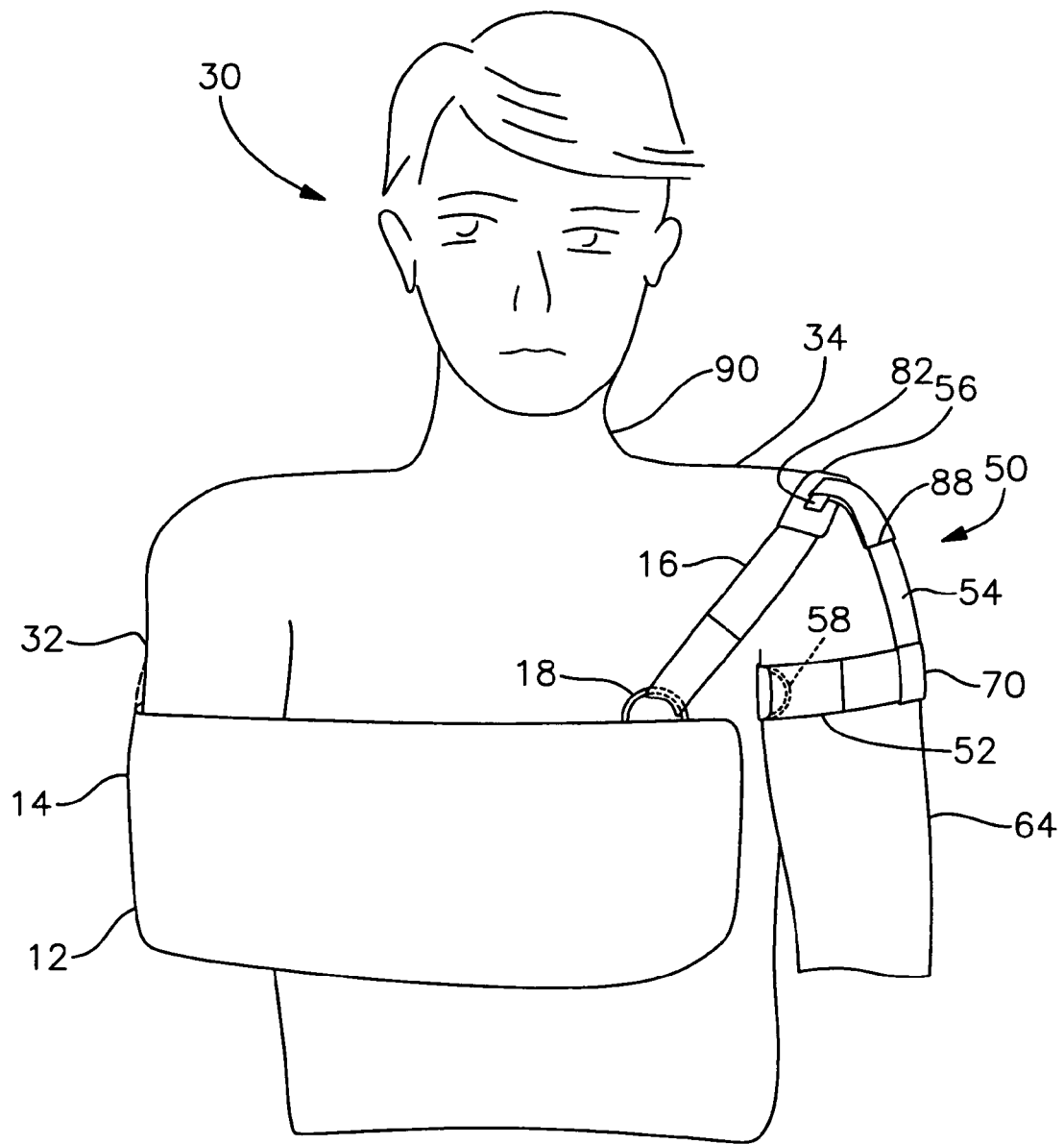
FIG. 2 is a front elevational view of a patient wearing an orthopedic sling in conjunction with one embodiment of the weight shifting constraint apparatus of this invention.

The present invention overcomes the foregoing problem in a simple and yet highly effective manner. As shown in FIG. 2, patient 30 likewise has an injured right arm 32 that is supported within the pouch 14 of a conventional orthopedic sling 12. A shoulder strap 16 is secured to ring 18 to suspend pouch 14 and supported arm 32 from the wearer's well shoulder 34. The opposite end of strap 16 is once again secured to a second ring carried at the top edge of pouch 14 and located generally behind arm 32.

The present invention utilizes an apparatus 50 for laterally constraining shoulder strap 16 so that the shoulder strap is held away from the wearer's neck and the weight of supported arm 32 is shifted laterally outwardly onto the much stronger and more supportive shoulder muscles of well shoulder 34. Apparatus 50 includes an armband 52, an anchor strap 54 and a cushioning pad 56, shown individually in FIGS. 3, 4 and 5, respectively. Armband 52 and strap 54 preferably comprise a flexible lightweight material similar to the material that composes a conventional shoulder strap 16 of sling 12. Various types of materials (e.g. synthetic fabrics, cloth, leather, etc.) may be employed within the scope of this invention. Cushioning pad 56 preferably includes a durable foam or other elastomeric material analogous to that employed for conventional cushioning pads commonly featured in orthopedic sling shoulder straps.

As best shown in FIG. 3, armband 52 carries a metal D-ring 58 at one end thereof. Typically, the armband is stitched to include a transverse channel through which the D-ring is installed. A complementary two-part connector is incorporated into or otherwise carried by at least one side of armband 52. For example, the armband may include a hook material connector 60 proximate the end of the armband that is opposite D-ring 58. The remaining length of armband 52 incorporates or otherwise carries a loop material connector 62. As shown in FIG. 2, armband 52 is wrapped longitudinally about the well arm 64 of patient 30. The end of the armband carrying hook material 60 is then pulled through ring 58 and pulled back to tighten the armband about the arm. The hook material is then engaged with (e.g. pressed against) loop material 62 to secure the armband firmly in place on the wearer's well arm 64.

Figure 6:
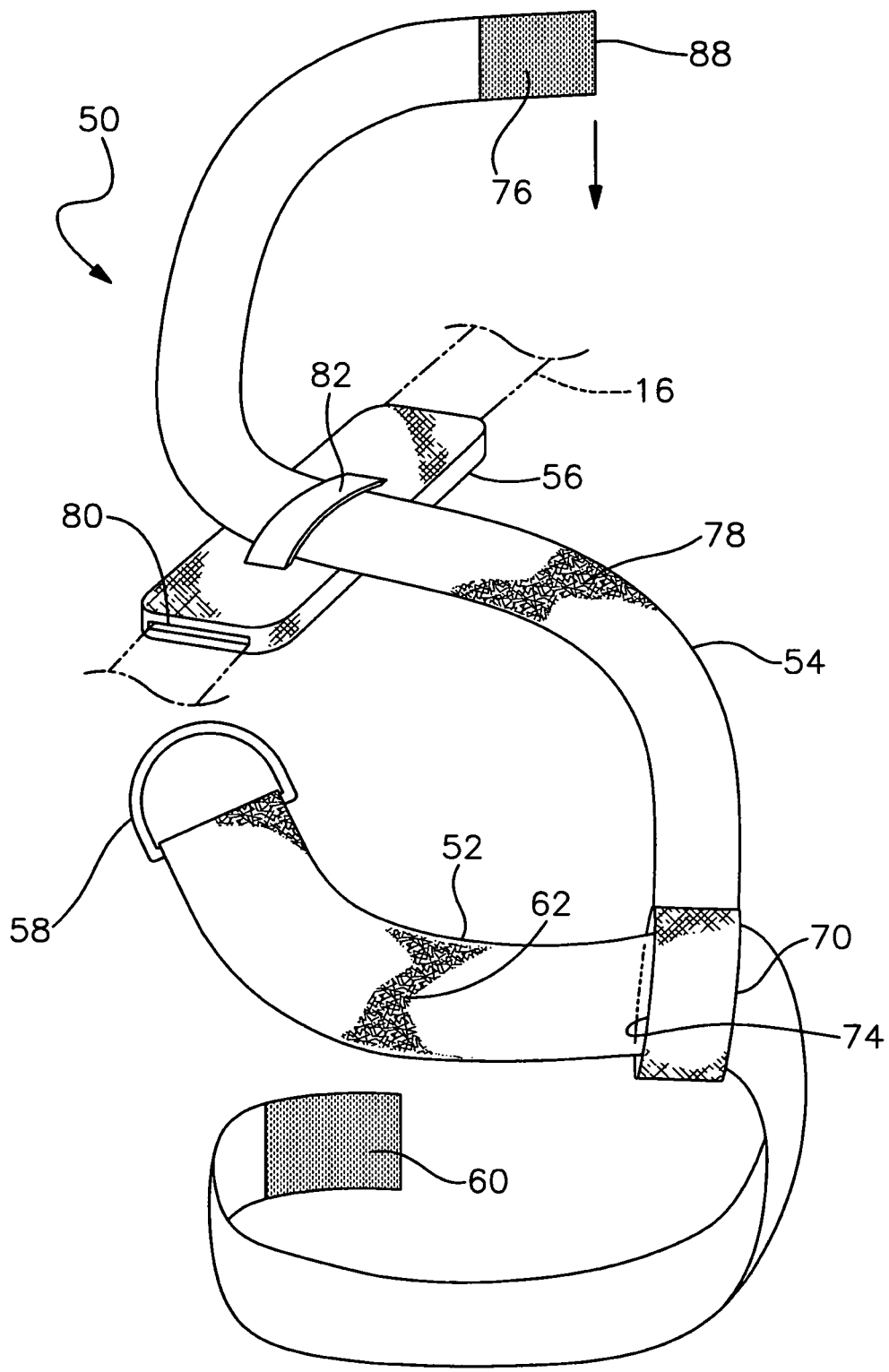
FIG. 6 is a perspective view of the apparatus with the components interengaged; the anchor strap and armband are not yet closed and are left open to more clearly illustrate the interengagement of those components with each other and with the cushioning pad.

Anchor strap 54, shown alone in FIG. 4, carries an integral sleeve 70 at its lower end. This sleeve may be formed by simply folding over the distal end of strap 54 and stitching or otherwise securing that end to strap 54 along line 72 to form sleeve 70. The sleeve includes a transverse opening 74. As shown in FIG. 6, armband 52 is slid longitudinally through opening 74 of sleeve 70. This interengages the lower end of anchor strap 54 to armband 52. An opposite upper end of strap 54 incorporates or otherwise carries a connector component 76, FIGS. 4 and 6, which may again comprise one part of a standard hook and loop connector pair (e.g. a hook portion). The body of strap 54 between hook connector 76 and sleeve 70 incorporates or carries loop connector material 78. This allows the anchor strap to be fastened to itself by interengaging connector components 76 and 78 in a standard manner. It should be understood that alternative types of fasteners (e.g. snaps, fasteners, clips, etc.) may be utilized. Such alternative fastening means may also be employed for the armband.

The upper end of anchor strap 54 is interconnected to cushioning pad 56, shown alone in FIG. 5. This pad is secured to shoulder strap 16, FIGS. 2 and 6, in a manner analogous to that by which conventional cushioning pads are secured to the shoulder straps of conventional orthopedic slings. Pad 56 may include a longitudinal channel or slot 80, FIG. 6, through which strap 16 is inserted. Apparatus 50 modifies the standard cushioning pad somewhat by including a separate loop component 82 that is secured to underlying pad 56. Loop 82 may be formed from a flexible fabric material or alternatively formed unitarily with or connected integrally to pad 56. The loop may alternatively comprise a metal or plastic ring that is joined to pad 56. In any event, as shown in FIG. 6, loop 82 accommodates anchor strap 54. The anchor strap is inserted through loop 82 and folded against itself such that hook connector 76 interengages and is secured to loop connector 78. The upper end 88 of strap 54 is secured to the body of the strap as shown in FIGS. 2 and 6. The anchor strap therefore forms or defines an upper loop that interengages loop 82 carried by pad 56. As a result, the anchor pad is securely interconnected between the cushioning pad at its upper end and the closed armband at its lower end.

With each of the components 52, 54 and 56 of apparatus 50 assembled, interconnected and worn by the patient, the apparatus is in the condition generally shown in FIG. 2. Therein, apparatus 50 constrains shoulder strap 16 (which is inserted through pad 56) laterally away from the side of patient's neck 90. Instead, the shoulder strap 16, and therefore the weight of the patient's supported arm 32 are shifted and borne laterally outwardly along the shoulder 34 by the muscles of that shoulder. This is a much more comfortable position for bearing the weight of the sling and the supported arm 32. Severe neck discomfort, neck strain and potential injury to the neck muscles are thereby avoided. At the very least, the patient's comfort is improved considerably.

In addition to improving patient comfort, apparatus 50 provides a number of additional benefits. The constraint apparatus features a fairly simple, inexpensive and easy to use construction. The apparatus may be attached to the shoulder strap of virtually any standard medical or orthopedic sling in a quick and convenient manner. The armband and anchor strap components are secured in place quickly and conveniently by easy to use and reliable hook and loop connectors. The sleeve 70 at one end of anchor strap 54, as well as the complementary loops interconnecting the upper end of the anchor strap and the cushioning pad allow the apparatus 50 to be adjusted in size and positioned quickly and conveniently so that the sling strap 16 is pulled away from the neck and held upon the more supportive shoulder of virtually any person. This allows the apparatus to be used effectively for persons having various sizes and builds.

Apparatus 50 is positioned effectively, yet unobtrusively on the wearer's well arm. This is unlike any apparatus of the prior art. There is no interference from the apparatus with the patient's injured arm. By the same token, the apparatus employs a simple construction without complex, bulky or cumbersome straps and braces. The patient is free to move his or her torso. Moreover, apparatus 50 does not interfere with the patient's use of his or her well arm. The patient is free to move and able to perform a variety of activities without interference from apparatus 50.

The use of reliable hook and loop connectors holds the shoulder strap 16 securely in place laterally outwardly from the neck and upon shoulder 34. If the connectors do gradually loosen, they are easy to readjust and reposition so that comfortable support of the sling is maintained. In any event, anchor strap 54 is pulled sufficiently to constrain pad 56 and attached strap 16 well away from the side of neck 90. This provides for significantly improved comfort, particularly when the sling must be worn for extended periods of time.

It should be understood that a number of the features of the weight shifting apparatus may be varied within the scope of the invention. For example, in some versions the cushioning pad and attached loop may be omitted and the anchoring strap may be secured directly to the conventional shoulder strap of the sling. "Anchor strap" should be construed broadly and may include various other types, sizes and shapes of anchoring pieces (flexible and rigid or relatively inflexible). Various alternative means may be employed for fastening the armband to the patient's well arm. In certain embodiments, multiple anchor straps may be interconnected between the shoulder strap of the sling and the armband. The anchoring components may be located at various positions about the arm interconnecting the shoulder strap and the armband. In all versions, the shoulder strap is constrained laterally outwardly from the patient's neck by one or more anchor straps or anchoring pieces that are secured to an armband that encircles the well arm.

Figure 7:
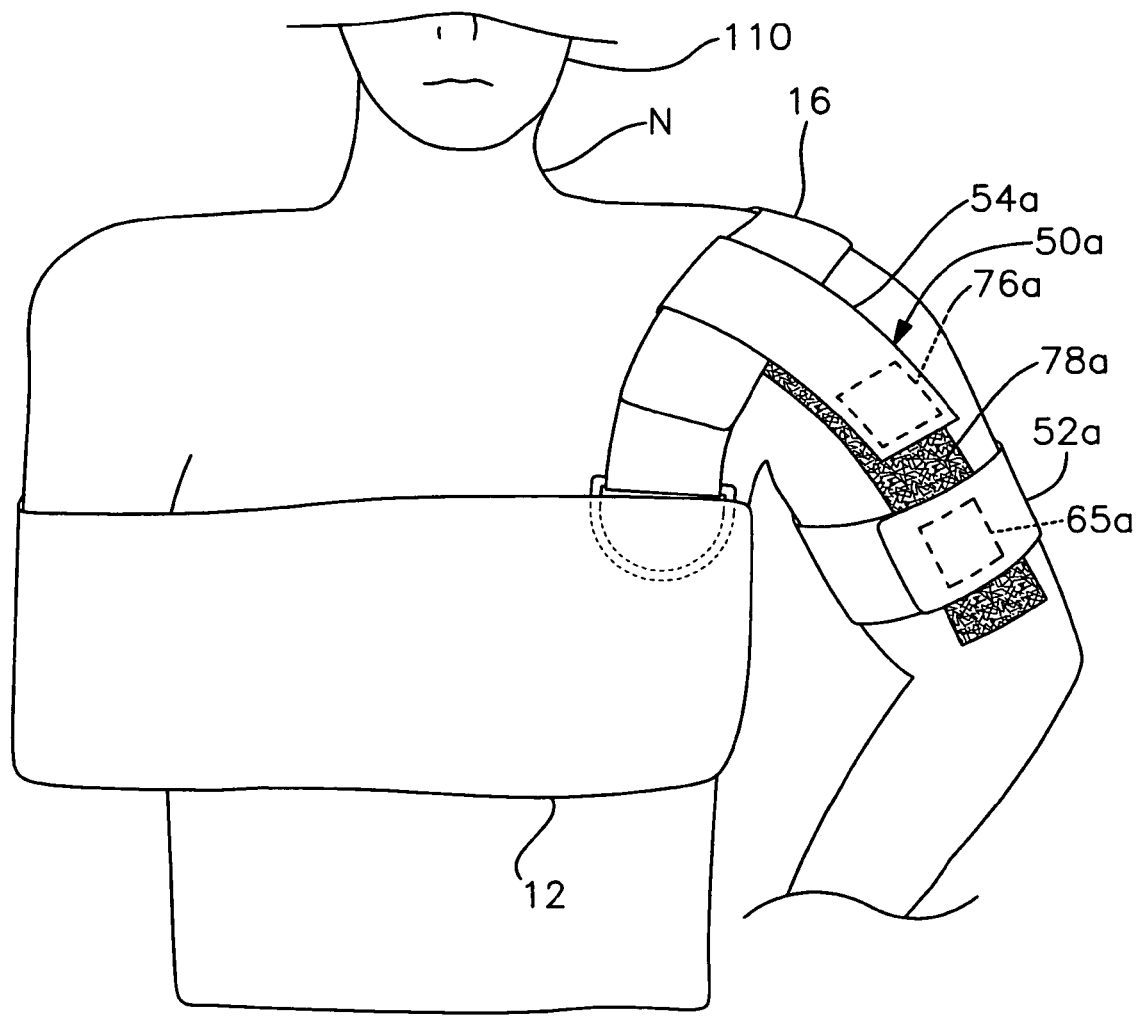
FIG. 7 is a front elevational view of a patient wearing an orthopedic sling that is laterally adjusted by an alternative preferred weight shifting constraint apparatus in accordance with this invention.

There is shown in FIG. 7 an alternative preferred apparatus 50a for laterally constraining the shoulder strap 16 away from the neck of wearer 110. Apparatus 50a includes an armband 52a, which again wraps about the user's upper arm and a connective anchor strap 54a that joins the armband to sling strap 16. In this version, the previously described cushioning pad is eliminated. As in the prior embodiment, armband 52a and strap 54a preferably comprise flexible, lightweight material, which may be cushioned or padded so that it is comfortable for wearer 110. Various types of material (e.g. synthetic and natural fabrics, foam, cloth, leather, etc.) may be employed within the scope of this invention. It is particularly convenient for anchor strap 54a to include a durable foam or other elastomeric material so that the strap is cushioned as it extends across the wearer's shoulder and upper arm.

Figure 8:
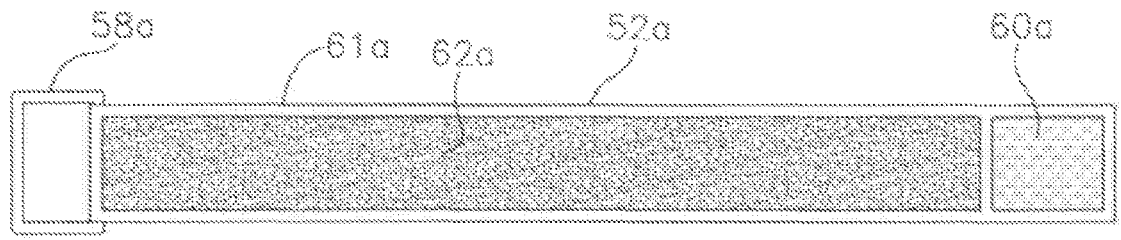
FIG. 8 is an elevational view of the exterior surface of a preferred armband used in the version of FIG. 7.
Figure 9:
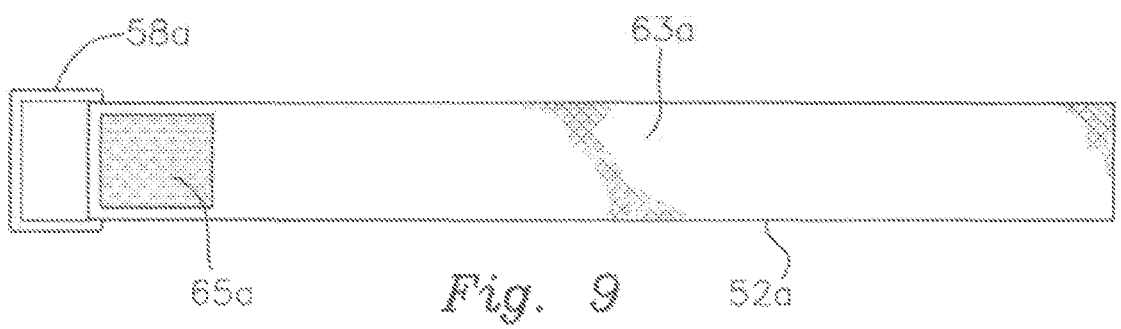
FIG. 9 is an elevational view of the inner surface of the armband of FIG. 8.

One version of armband 52a is illustrated alone in FIGS. 8 and 9. An outer surface 61a of armband 52a carries an elongate strip of a Velcro® loop material 62a, which is fastened to surface 61a by stitching, adhesive, etc. A complementary piece of Velcro® hook material 60a is carried by outer surface 61a adjacent to loop material 62a and adjacent one end of armband 52a. A buckle 58a (which may alternatively comprise a D-ring as shown in the previously described embodiment) is attached at the opposite, second end of armband 52a. This buckle is typically secured to the armband in a manner analogous to that previously described for D-ring 58 in FIG. 3.

As depicted in FIG. 9, the opposite, inner surface 63a of armband 52a carries a second piece of Velcro® hook material 65a that is secured adhesively, by stitching, etc. to the inner surface adjacent to buckle 58a. The remaining length of surface 63a is not covered by any type of complementary hook or loop connective material. Rather, inner surface 63a preferably comprises a synthetic or natural fabric or cloth-like material that may be worn comfortably by the user when wrapped about and engaging the user's arm.

Armband 52a is wrapped about and secured to the well arm of the patient in a manner similar to that previously described. In particular, armband 52a is wrapped about the user's well or "good" arm such that inner surface 63a comfortably engages that arm. The wearer or an assistant then inserts the distal end of the armband (i.e. the end carrying hook material 60a) through buckle 58a and pulls back the distal end until the armband is cinched as snugly as desired. The hook material 60a proximate the distal end of the armband is then pressed against the underlying loop material 62a carried by the outer surface 61a of armband 52a. This secures the wrapped armband in place about the wearer's uninjured arm.

Figure 10:
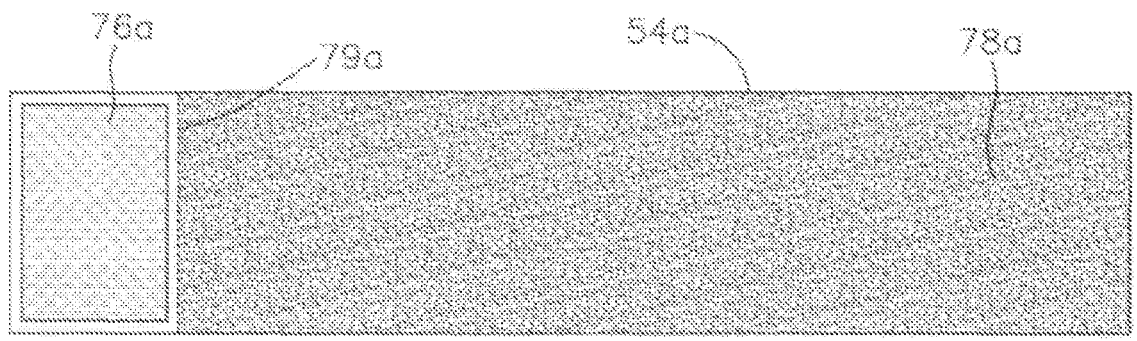
FIG. 10 is an elevational view of the anchoring strap used in the embodiment of FIG. 7 and particularly depicting the complementary hook and loop connectors carried by that strap.

Anchoring strap 54a is shown alone in FIG. 10. As previously indicated, strap 54a is preferably cushioned or padded for most, if not all, of its length. The side of strap 54a that is shown in FIG. 10 carries a Velcro® loop material 78a for most of the strap's length. A piece of Velcro® hook material 76a is attached to the strap immediately adjacent loop material 78a and proximate one end of the connective strap. A transverse stitch 79a is formed across the strap such that hook material 76a is mounted upon a relatively thin end of the anchor strap. This renders the hook material at the end of the strap easier to manipulate and interengage with the complementary loop material 78a when the apparatus 50a is fully assembled in the manner that will be described more fully below. Once again, hook material 76a may be fastened to the connecting strap by appropriate stitching, adhesives, etc. The complementary loop material 78a may be formed integrally in the cover or other outer surface of the anchor strap. Alternatively, the loop material 78a may be fastened to the surface of the anchor strap by various known attachment means as previously described. As also previously described, a cushioning foam or padding may be contained within the anchor strap.

Apparatus 50a is assembled and secured on the patient quickly and conveniently in order to effectively constrain shoulder strap 16 of orthopedic sling 12 away from the neck and related area of the trapezius muscle of the user. This is specifically accomplished in the following manner.

Initially, anchor strap 54a is fastened to armband 52a. This is achieved by extending strap 54a transversely across inner surface 63a of armband 52a. Loop connector surface 78a is aligned with hook connector 65a and the complementary hook and loop connective pieces are interengaged to releasably fasten anchor strap 54a to the inside surface 63a of armband 52a. The armband is then wrapped about and fastened upon the upper arm of the wearer in the manner previously described and as shown in FIG. 7.

Anchor strap 54a is next inserted beneath sling shoulder strap 16. See FIG. 7. The distal end of strap 54a (i.e. the end bearing hook connector piece 76a) is wrapped about sling strap 16 and interengaged with the loop material connector 78a carried by the outwardly facing surface of strap of 54a. In particular, hook piece 76a releasably interengages loop material 78a so that the anchor strap 54a forms an upper loop about sling strap 16. This loop is effectively secured to the armband by the hook and loop interconnection formed between the hook material 65a of armband 52a and the loop material 78a of anchor strap 54a. The armband thereby pulls or constrains sling strap 16 laterally away from the wearer's neck. Apparatus 50a maintains the position of the sling strap proximate the outer end of the wearer's shoulder. As a result, the weight of the sling and the injured arm supported thereby are borne by the much stronger shoulder muscles. This is a much more comfortable and less stressful position, which contributes considerably to the wearer's comfort and rehabilitative progress. Undue neck strain and risk of injury are reduced as previously described.

Figure 11:
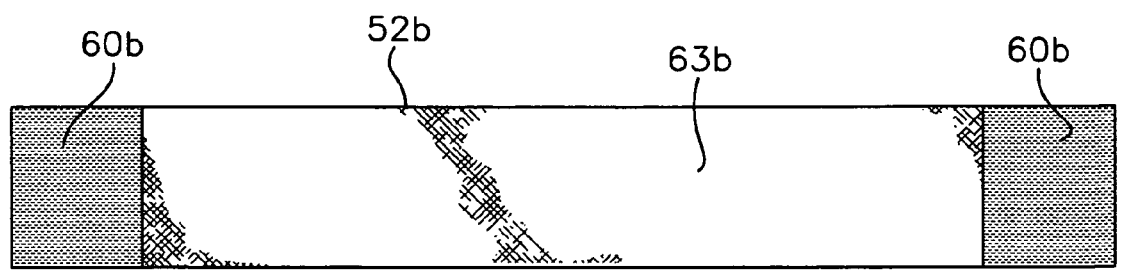
FIG. 11 is an elevational view of the inside surface of an alternative armband, which may be employed in the embodiment of the apparatus shown in FIG. 7.
Figure 12:
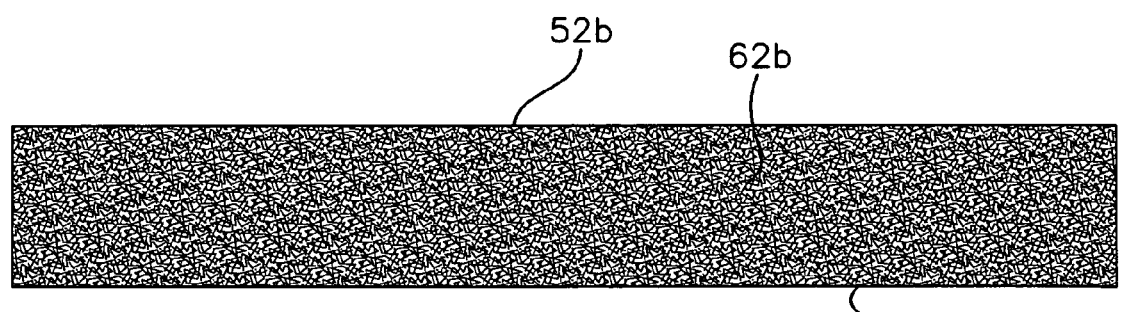
FIG. 12 is an elevational view of the outer surface of the armband of FIG. 11.

In yet another embodiment, shown in FIGS. 11 and 12, an even simpler armband 52b may be employed for an apparatus otherwise analogous to apparatus 50a. In this version, the armband again comprises an elongate strap or band that is wrapped about and secured to the user's arm. However, a buckle or D-ring is eliminated. The inner surface 63b instead carries a pair of connective Velcro® hook elements 60b proximate respective ends of the strap. By the same token, the outer surface of armband 52b comprises a connective Velcro® loop material 62b, FIG. 12, which extends for most if not the entire length of the outer surface of the strap. Armband 52b may be otherwise constructed in a manner analogous to the previously described straps of this invention.

Armband 52b cooperates with anchor strap 54a in a manner analogous to that shown in FIG. 7. In particular, the loop material 78a of anchor strap 54a is releasably interengaged with one of the hook elements 60b of armband 52b such that the anchor strap 54a is releasably fastened and extends transversely to armband 52b. The apparatus is then engaged with the wearer and the wearer's orthopedic sling in order to pull the shoulder strap of the sling away from the wearer's neck. First, armband 52b is secured to the wearer's well arm by wrapping the armband about the biceps or upper portion of the arm such that inner surface 63b faces the arm. This exposes loop material 62b on the outer surface of the armband. The armband is wrapped as loosely or tightly as is required to provide a comfortable fit about the arms. The other hook element 60b (i.e. the hook element that is not releasably engaged with anchor strap 54a) is then pressed against the loop material 62b to releasably secure the armband 52b in place about the wearer's well arm.

After the armband is secured, the anchor strap is engaged with the strap of the orthopedic sling and fastened in place in a manner analogous to that previously described. In particular, the distal end of the anchor strap (i.e. the end bearing hook element 76a) is inserted under the sling strap 16 and looped about the strap. Hook element 76a is then pressed against loop material 78a of strap 54a to secure the weight shifting apparatus in place in a fashion similar to that shown in FIG. 7.

In each of the embodiments, the armband effectively pulls the sling strap outwardly on the shoulder so that irritation to the neck and trapezius muscle are significantly reduced.

From the foregoing it may be seen that the apparatus of this invention provides for an apparatus for shifting or transferring the weight of an arm supported by an orthopedic sling so that such weight is borne largely by the shoulder rather than the neck of the wearer. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

Other embodiments will occur to those skilled in the art and are within the following claims.

What is claimed is:

1. A weight shifting orthopedic sling apparatus for use by a wearer having an injured arm an opposite well arm, and a well arm shoulder interconnecting the wearer's well arm and neck, said apparatus comprising:

a sling having a pouch for supporting the wearer's injured arm and a shoulder strap attached to said pouch for extending across the wearer's well arm shoulder;

an armband for encircling and attaching to the well arm of the wearer; and an anchor strap interconnected between said armband and said shoulder strap for extending across the well arm and well arm shoulder of the wearer, said anchor strap forming a loop that wraps completely around and encircles said shoulder strap and said anchor strap having a lower end portion attached to said armband whereby said anchor strap pulls said shouler strap laterally away from the wearer's neck and constrains said shoulder strap to extend across the well arm shoulder such that at least a majority of the weight of the supported injured arm is borne by the well arm shoulder rather than the neck of the wearer.

2. The apparatus of claim 1 in which said anchor strap is releasably secured to said shoulder strap and includes a first set of complementary releasable connectors carried by a common side of said anchor strap, whereby said anchor strap is inserted beneath and wrapped completely around said shoulder strap and said first set of complementary releasable connectors are interengaged to form said loop for releasably securing said anchor strap to said shoulder strap.

3. The apparatus of claim 2 in which said armband and said anchor strap include a second set of complementary connectors for releasably securing said anchor strap to said armband such that said anchor strap extends transversely to said armband.

4. The apparatus of claim 3 in which said second set of complementary connectors include hook material carried by one of said armband and said anchor strap and loop material carried by a corresponding one of said armband and said anchor strap.

5. The apparatus of claim 1 in which said armband includes a first side carrying an elongate strip of connective loop material that extends from proximate a first end of said armband and a complementary connective hook element disposed between said elongate strip of connective loop material and an opposite distal end of said armband, said armband further carrying a buckle proximate the first end thereof, said opposite distal end of said armband being inserted through said buckle and pulled back to engage said complementary connective hook element with said elongate strip of loop material to secure said armband about a wearer's upper arm.

6. The apparatus of claim 5 in which said armband includes an opposite side that carries a second connective hook element adjacent to said first end of said armband, said second connective hook element being interengaged by a complementary loop connector carried by said anchor strap to releasably secure said anchor strap to said armband.

7. The apparatus of claim 1 in which said armband includes a first inner surface that has a pair of hook connector elements at respective ends thereof and an opposite exterior surface that includes an elongate strip of complementary loop connector material, said armband being wrapped about a wearer's arm such that one of said hook connector elements is releasably engageable with said elongate strip of complementary loop connector material to secure said armband about the wearer's arm.

8. The apparatus of claim 7 in which said anchor strap carries a connective loop element that is engageable with the hook connector element carried by said armband to secure the anchor strap to the armband such that the anchor strap extends generally transversely to the armband.

9. The apparatus of claim 1 in which said armband includes complementary releasable connector components that are interengaged to secure the armband about a wearer's well arm.

10. The apparatus of claim 9 in which said complementary releasable connector components carried by said armband include complementary hook and loop connectors.

11. The apparatus of claim 2 in which said first set of complementary releasable connectors carried by said anchor strap include complementary hook and loop connectors.

12. The apparatus of claim 1 in which said armband is connected to said anchor strap by a sleeve carried by a lower end of said anchor strap, said armband being inserted longitudinally through said sleeve such that said anchor strap is adjustable longitudinally along said armband.

13. The apparatus of claim 2 in which said armband is connected to said anchor strap by a sleeve carried by a lower end of said anchor strap, said armband being inserted longitudinally through said sleeve such that said anchor strap is adjustable longitudinally along said armband.

14. The apparatus of claim 1 in which said loop of said anchor strap includes a first segment extending across and above said shoulder strap and a second segment attached to said first segment and extending across and beneath said shoulder strap.

15. The apparatus of claim 14 in which said first segment and an intermediate portion of said anchor strap between an upper end portion and said lower end portion include a first set of complementary releasable connectors carried by a common side of said anchor strap, whereby said anchor strap is inserted beneath and wrapped about said shoulder strap and said first set of complementary releasable connectors are interengaged to form said loop for releasably securing said anchor strap to said shoulder strap.

* * * * *